United States Patent [19]

Herring

[11] Patent Number: 5,002,526
[45] Date of Patent: Mar. 26, 1991

[54] TAMPON APPLICATOR
[75] Inventor: Laura E. Herring, Decatur, Ga.
[73] Assignee: Kimberly-Clark Corporation, Neenah, Wis.
[21] Appl. No.: 456,016
[22] Filed: Dec. 22, 1989
[51] Int. Cl.$^5$ .............................................. A61F 13/20
[52] U.S. Cl. ...................................... 604/11; 604/15; 604/364
[58] Field of Search .......................... 604/11, 13–18, 604/364, 904

[56] References Cited

U.S. PATENT DOCUMENTS

| | | | |
|---|---|---|---|
| 2,518,486 | 8/1950 | Mende | 128/261 |
| 3,563,244 | 2/1971 | Asaka | 604/364 |
| 3,724,462 | 4/1973 | Hanke | 128/263 |
| 3,859,125 | 1/1975 | Miller et al. | 604/364 |
| 3,882,196 | 5/1975 | Hanke | 260/895 |
| 3,882,869 | 5/1975 | Hanke | 128/263 |
| 3,911,917 | 10/1975 | Hanke | 128/263 |
| 3,954,104 | 5/1976 | Kraskin et al. | 128/263 |
| 4,099,976 | 7/1978 | Kraskin et al. | 106/15 R |
| 4,317,447 | 3/1982 | Williams | 604/364 |
| 4,372,311 | 2/1983 | Potts | 128/287 |
| 4,503,098 | 5/1985 | Potts | 427/394 |
| 4,618,648 | 10/1986 | Marten | 525/60 |
| 4,618,649 | 10/1986 | Ofstead | 525/60 |
| 4,656,216 | 4/1987 | Muller et al. | 524/381 |
| 4,675,360 | 6/1987 | Marten | 525/60 |
| 4,708,999 | 11/1987 | Marten | 526/320 |
| 4,772,663 | 9/1988 | Marten et al. | 525/60 |
| 4,900,299 | 2/1990 | Webb | 604/11 |
| 4,931,501 | 6/1990 | Lai et al. | 525/61 |

FOREIGN PATENT DOCUMENTS 0291024 11/1988 European Pat. Off. .
88/2776 4/1988 South Africa .

Primary Examiner—C. Fred Rosenbaum
Assistant Examiner—Sharon Rose
Attorney, Agent, or Firm—William E. Maycock

[57] ABSTRACT

A tampon applicator which is biodegradable and water-dispersible is provided. The applicator is formed by injection molding a modified poly(vinyl alcohol) which is self-plasticizing. In certain preferred embodiments, the modified poly(vinyl alcohol) has the following structure:

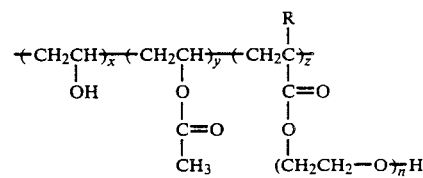

in which R is hydrogen or methyl, n is a number from 1–1,000, x is 50–99.9 mole percent, y is 0–50 mole percent, and z is 0.001–50 mole percent. Tampon applicators made from this material have been found to be rapidly dispersible in water, to support heavy fungal growth, and to have a commercially acceptable outer surface, i.e., a surface which is not sticky, slippery, or slimy prior to contact of the applicator with water.

10 Claims, No Drawings ive TAMPON APPLICATOR

BACKGROUND OF THE INVENTION

1. Field of the Invention

This invention relates to injection-molded and extruded tampon applicators and in particular to injection-molded and extruded tampon applicators which are water-dispersible and biodegradable. More specifically, the invention relates to injection-molded and extruded tampon applicators made from a modified poly(vinyl alcohol) which is self-plasticizing.

2. Description of the Art

The standard construction for a tampon applicator is a pair of telescoping tubes, the outer tube carrying the tampon's absorbent material (the tampon's "pledget") and the inner tube serving as a plunger for dispensing the pledget. Tampon applicators in current commercial use are typically made from either a plastic or paper-based material. Plastic tampon applicators are preferred by many women since they can be molded to include a grip ring and a petal-shaped forward end which aids in the insertion of the device and in retaining and protecting the pledget while it is in the outer tube. Plastic tampon applicators are typically made from polyethylene using an injection-molding process.

A convenient place to dispose of a tampon applicator is in a toilet bowl, even though all of the currently used plastic applicators are ill-suited for such disposal. While such applicators will flush, they settle in septic tanks without decomposing. Moreover, they accumulate on the screens in waste-water treatment plants, creating blockages. If the screens don't stop them, they escape into the environment intact, often washing up on beaches. Because plastic tampon applicators typically neither float on the surface nor settle to the bottom of settling tanks, they are not removed as sludge or by skimmers. In view of such environmental and esthetics considerations, it is thus highly desirable that the plastic applicator be water-dispersible and biodegradable. Such properties have not yet been achieved commercially, in spite of efforts to achieve these properties for a plastic-based material which have been on-going for at least the past forty years.

An early patent in this area is U.S. Pat. No. 2,518,486 to William Mende. Although not specifically a tampon applicator, the Mende patent describes a device for dispensing pharmaceutical preparations into body cavities which includes an outer tube and a plunger. To avoid problems with clogging of toilets, Mende suggests forming his device from a synthetic material which will soften and swell upon contact with water, such as a poly(vinyl alcohol).

U.S. Pat. No. 3,882,869 to David Hanke discusses Mende's poly(vinyl alcohol) proposal and concludes that Mende's approach is unworkable in a commercial environment because the poly(vinyl alcohol) becomes unstable in the presence of moisture laden air, becomes prematurely sticky in contact with moist surfaces, and is costly to fabricate since it must be cast from solution and then molded to shape (see Hanke at column 1, lines 48–59). As an alternative to Mende's approach, Hanke suggests using a polyethylene oxide polymer or hydroxypropyl cellulose containing between about 50 and about 75 percent by weight of a filler such as talc.

In another of his patents (U.S. Patent 3,724,462), Hanke discloses a further approach for using water-soluble polymers in the preparation of tampon applicators. In accordance with this patent, the inner and outer tubes of the applicator are made of different water-soluble polymers which are incompatible with one another. In this way, problems with the tubes fusing together under high humidity/high temperature conditions are avoided. Poly(vinyl alcohol) polymers were again studied in this patent and it was observed that this polymer developed a sticky surface when subjected to a temperature of about 120 degrees F (about 49 degrees C) and a relative humidity of about 90 percent.

In addition to being sticky, tampon applicators made from poly(vinyl alcohol) polymers also suffer from odor problems; specifically, they can have an acetic acid smell. Hanke U.S. Patent Nos. 3,911,917 and 3,882,196 address this problem by mixing a proton acceptor such as calcium carbonate with the poly(vinyl alcohol) polymer before the polymer is injection molded to form the applicator.

A recent patent application in this area is South African application Serial No. 87/3135 to Carlton Paper of South Africa, Limited. This application describes the injection molding of a mixture of partially hydrolyzed poly(vinyl alcohol) (80 percent by weight) and a plasticizer (20 percent by weight) to produce tubes for tampon applicators. Poly(vinyl alcohol) cross-linked with an aldehyde is described as an alternative material but was not employed in either of the two examples.

The need for 20 percent by weight plasticizer shows that the hydrolyzed poly(vinyl alcohol) used by Carlton Paper was not truly a thermoplastic resin. Also, the use of a plasticizer at these levels can be expected to result in increased moisture sensitivity, decreased tensile strength, and migration of the plasticizer from the finished product so as to produce a slimy or slippery outer surface. In addition, as is typical of conventional poly(vinyl alcohol)s, Carlton Paper's device exhibited a slow dissolution rate in cold water. Specifically, Carlton Paper reported in its South African application that 16 hours were required to dissolve a hollow tube of its externally-plasticized material in cold water. The tube had a wall thickness of one millimeter.

Poly(vinyl alcohol) polymers are also suggested for use in tampon applicators in Potts' U.S. Pat. No. 4,372,311. This patent discloses a two-layer material wherein a watersoluble polymer, e.g., a poly(vinyl alcohol), is coated with a non-water soluble, but biodegradable, polymer, e.g., a polycaprolactone.

Examples of efforts to use materials other than poly(vinyl alcohol) to manufacture tampon applicators which are water-dispersible and/or biodegradable can be found in Kraskin et al., U.S. Pat. Nos. 3,954,104 and 4,099,976 (hydroxyalkyl cellulose) and in European Patent Publication No. 291,024 [poly(3-hydroxybutyric acid)].

SUMMARY OF THE INVENTION

The foregoing references show that there has been a continuing effort to use water-soluble plastic materials, poly(vinyl alcohol) in particular, in tampon applicators. Notwithstanding these efforts, a truly suitable material has not been found. Accordingly, it is an object of this invention to provide such a material. More particularly, it is an object of the present invention to provide a tampon applicator which is made from a thermoplastic material which is (1) injection moldable or extrudable, (2) water-dispersible, and (3) biodegradable. It is also an object of the present invention to provide such an applicator which is strong, flexible, economical, and which has commercially acceptable surface characteristics, i.e., which is not sticky, slippery, or slimy. More particularly, the present invention provides a tampon applicator comprising at least one elongated tubular member prepared from an injection-moldable or extrudable material which includes a poly(vinyl alcohol) which has been modified so that it is self-plasticizing, said tampon applicator being water-dispersible and biodegradable.

The present invention achieves the foregoing and other objects by providing a tampon applicator made from an injection-moldable and extrudable material which includes a poly(vinyl alcohol) which has been modified so that it is self-plasticizing. In this way, the applicator can be formed by injection molding or extrusion without the need for high levels of external plasticizers such as the 20 percent by weight glycerine level used in the Carlton Paper patent application discussed above.

As used herein, the term "poly(vinyl alcohol)" is intended to include any polymer at least 50 percent of which on a mole basis comprises the structure -(-CH2CHOH-)x-, in which x represents the number of repeating units. For convenience, poly(vinyl alcohol)s which have been modified to be self-plasticizing will be referred to herein as "modified, self-plasticizing poly(vinyl alcohol)s" or simply "modified poly(vinyl alcohol)s".

A preferred modified, self-plasticizing poly(vinyl alcohol) for use in preparing the tampon applicators of the present invention is represented by the following structural formula:

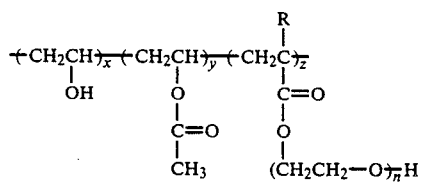

in which R is hydrogen or methyl, n is a number from 1–1,000, x is 50–99.9 mole percent, y is 0–50 mole percent, and z is 0.001–50 mole percent.

As demonstrated in the examples presented below, by using polymers of the above type, tampon applicators have been prepared which (1) disperse in distilled or ocean water in less than one hour, (2) are rapidly biodegraded, and (3) have excellent, commercially acceptable outer surfaces.

DETAILED DESCRIPTION OF THE INVENTION

As already stated, the present invention provides a tampon applicator comprising at least one elongated tubular member prepared from an injection-moldable or extrudable material which includes a poly(vinyl alcohol) which has been modified so that it is self-plasticizing, said tampon applicator being water-dispersible and biodegradable.

So as to avoid the need for high levels of external plasticizers, the materials used to prepare the tampon applicators of the present invention preferably should have a viscosity at the molding or extrusion temperature, e.g., at about 195 degrees C, of between about 2,500 and about 4,500 poise at a shear rate of 200 sec$^{-1}$ and of between about 500 and about 800 poise at a shear rate of 4,000 sec$^{-1}$. By having viscosities in this range, the materials can be injection molded or extruded using conventional equipment either without the use of an external plasticizer or with relatively low levels of such a plasticizer. Some level of external plasticizer may be desired to enhance flexibility but is not required to ensure thermoplastic stability as is the case in the South African Carlton Paper patent application.

In addition to the foregoing viscosity characteristics, the materials used to prepare the tampon applicators of the present invention should be biodegradable and water-dispersible. In certain preferred embodiments, the materials are sufficiently water-dispersible so that finished applicators, having wall thicknesses of 25 mils or less, have water dispersion times of less than 2 hours and preferably less than 1 hour. Significantly, these dispersion times are achieved while at the same time providing an applicator whose outer surfaces are not sticky, slippery, or slimy prior to contact with water.

As discussed above, in accordance with the preferred embodiments of the invention, tampon applicators are prepared from a modified, self-plasticizing poly(vinyl alcohol) represented by the following structural formula:

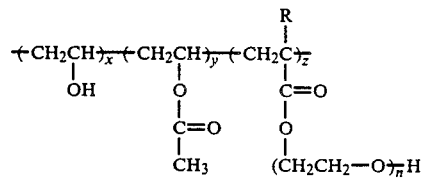

where R, n, x, y and z have the values given above.

A modified poly(vinyl alcohol) of this type can be produced by polymerizing a polyethylene oxide acrylate with vinyl acetate and then hydrolyzing the resulting product to produce pendant alcohol groups. The polyethylene oxide residues in the polymer provide the desired internal plasticizing function which allows the polymer, as well as blends of the polymer with fillers, pigments, and the like, to be injection or extrusion molded without significant amounts of an external plasticizer. Since complete hydrolysis seldom is achieved, the ratio of pendant hydroxy groups to pendant acetate groups typically is referred to as the degree of hydrolysis, expressed as a percentage.

Poly(vinyl alcohol)s having this structure are manufactured by Air Products and Chemicals, Inc., of Allentown, Pennsylvania, and are sold under the VINEX trademark. Complete descriptions of methods for preparing these compounds can be found in a series of patents to Finn L. Martin and co-workers, namely, U.S. Patent Nos. 4,618,648, 4,675,360, 4,708,999, and 4,772,663, the relevant portions of which are incorporated herein by reference. A particularly preferred VINEX poly(vinyl alcohol) for use with the present invention is that which Air Products has identified by the number 2025.

Modified poly(vinyl alcohol)s having the above structure can be used alone or preferably with suitable fillers, pigments, odor maskers, and other similar materials conventionally used in the preparation of personal care products. Examples of fillers which can be used include talc, starch, clay, and the like. Pigments include titanium dioxide, zinc oxide, and the like. Suitable odor maskers include, among others, fragrances, calcium carbonate, sodium bicarbonate, zinc oxide, and the like (see U.S. Patent Nos. 3,882,196 and 3,911,917, discussed above). In general, the amount of filler in the final product will be from about zero to about 50 percent by weight; the amount of pigment, when used, will be from about zero to about 5 percent by weight; and the amount of odor masker, when used, will be from about zero to about 1 percent by weight.

In addition to the foregoing ingredients, relatively low levels of an external plasticizer, i.e., less than about 5 percent by weight, can be used if desired for particular applications. For example, the molding of tampon applicators having a particularly complex shape may be facilitated by the presence of an external plasticizer. Similarly, if extra flexibility is desired in the finished applicator, an external plasticizer can be added.

The modified poly(vinyl alcohol) and other ingredients preferably are combined by melt mixing. This can be done in connection with the molding process or it can be done by the manufacturer of the modified poly(vinyl alcohol). For example, as sold by Air Products, the VINEX 2025 poly(vinyl alcohol) referred to above is available either as virgin polymer or as blends.

Although the tampon applicator of the present invention can comprise a single elongated tubular member, in preferred embodiments the tampon applicator of the present invention comprises a pair of telescoping tubes, either or both of which can be straight or curved. If both tubes are curved, the radii of curvature can be the same or different, but most preferably the tubes will have a mating relationship with a common radius of curvature. The tubes can be prepared by injection molding, extrusion, or by both injection molding and extrusion. If both injection molding and extrusion are employed, the outer tube typically will be made by injection molding whereas the inner tube will be made by extrusion. Finally, either or both tubes can be made from the modified poly(vinyl alcohol) described herein.

The molding or extrusion of the modified poly(vinyl alcohol) in accordance with the present invention can be performed using conventional equipment in accordance with well-known procedures. The specific processing conditions employed will, of course, depend upon the specifics of the equipment and the molds or dies used. For a general discussion of injection molding, see Irvin I. Rubin, "Injection Molding," in Herman F. Mark et al., Editors, "Encyclopedia pf Polymer Science and Engineering," Volume 8, John Wiley & Sons, New York, 1987, pp. 102-138. For a general discussion of extrusion, see Georqe A. Kruder, "Extrusion," in Herman F. Mark et al., Editors, "Encyclopedia of Polymer Science and Engineering," Volume 6, John Wiley & Sons, New York, 1986, pp. 571-631.

For purposes of illustration, a typical injection molding apparatus comprises a rear zone into which the polymer is introduced, a central zone, a front zone, a nozzle, and the mold. With such an apparatus, typical injection molding process temperatures are as follows:

| Zone | Temperature | |
|---|---|---|
| | Deg. F. | Deg. C. |
| Nozzle | 375-380 | 191-193 |
| Front | 375-410 | 191-210 |
| Center | 365-400 | 185-204 |
| Rear | 290-380 | 143-193 |
| Mold | 85-120 | 29-49 |

Other typical processing conditions include an injection pressure on the order of 400-1900 psi, a holding pressure on the order of 400-1600 psi, and a hold time on the order of 1.5-2.0 seconds. Overall cycle times on the order of 10 seconds have been achieved for a modified poly(vinyl alcohol) of the foregoing structural formula, which compare favorably with the cycle times for tampon applicators made from the standard material, polyethylene.

Without intending to limit it in any manner, the present invention will now be further illustrated by the following examples.

EXAMPLE 1

Preparation of Tampon Applicators

Tampon applicator tubes having petal tips, a grip ring, and a wall thickness of 0.025 inch (about 0.6 mm) were injection molded using the VINEX 2025 resin discussed above. As supplied by the manufacturer, the resin blend included a modified, self-plasticizing poly(vinyl alcohol) of the formula given above, a filler, a pigment, and an odor masker. The resin blend was used directly as supplied.

The molding conditions employed were as follows (the apparatus utilized two central heating zones):

| Zone | Temperature | |
|---|---|---|
| | Deg. F. | Deg. C. |
| Nozzle | 374 | 190 |
| 2 (front) | 377 | 192 |
| 3 (center) | 366 | 186 |
| 4 (center) | 305 | 152 |
| 5 (rear) | 359 | 182 |
| Mold | 85-90 | 29-32 |

The injection pressure used was 400 psi, the holding pressure was 400 psi, and the hold time was 1.5 seconds. The injection speed was about 6 inches (about 15 cm) per second.

The resin was found to work successfully in all respects in the injection molding process. The applicator tubes had the proper color, flexibility, and surface characteristics for commercial use. In direct contrast to applicator tubes made from conventional externally plasticized polyvinyl alcohols, the outer surfaces of the tubes made in accordance with the invention were not sticky, slippery, or slimy prior to contact with water.

EXAMPLE 2

Flushability

Tampon applicators prepared in accordance with the procedures of Example 1 were tested for their flushability in a toilet.

Two types of toilets were used, each having a 3.5-gallon flush volume: a siphon-jet water-conserving toilet and a siphon-vortex water-conserving toilet. These types represent powerful (siphon-jet) and weak (siphon-vortex) flushing abilities available in common use.

A combination of one applicator, one pledget, and 18 standard toilet paper squares was flushed in each toilet; all of the items cleared the bowl on the first flush.

EXAMPLE 3

Dispersibility

Tampon applicators prepared in accordance with the procedures of Example 1 were tested for their water dispersibility in both distilled and ocean water. For comparison, a KOTEX SECURITY polyethylene outer tube of the same diameter was also tested as a control.

Three 600-milliliter beakers were used. The first beaker (beaker 1) contained 500 milliliters of distilled water, a stir bar having a length of 7.5 cm, and one of the tampon applicators of Example 1 having a weight of about 4.5 grams. The second beaker (beaker 2) contained the same components except that ocean water from the east coast of Florida was used instead of distilled water. Finally, the third beaker (beaker 3) had the same components as beaker 1 except that the applicator of the invention was replaced with the KOTEX tube.

The experiments were conducted at room temperature with the stirrer being rotated at a rate in the range of 160-200 revolutions per minute. The speed of rotation was the same for all three beakers. The results of these experiments were as follows. After 45 minutes, the applicator in beaker 1 had essentially completely dispersed with only a small bit of the grip ring remaining undissolved. The applicator in beaker 2 had also dispersed, but not to the same extent as the one in beaker 1. Specifically, the applicator in beaker 2 was in pieces but had not yet fully dissolved. No change was observed for the applicator in beaker 3.

After 1.5 hours, the applicator in beaker 1 had completely dispersed, and the one in beaker 2 had dispersed except for the grip ring which was in pieces. Again, no change was observed for the applicator in beaker 3.

These results clearly show that tampon applicators of the present invention are fully dispersible in both distilled and ocean water in a period of less than 2 hours, with the dispersion in distilled water being somewhat faster than the dispersion in ocean water. The results also show that the applicators are substantially completely dispersed in less than one hour in distilled water. The distilled water test is considered representative of the behavior of the applicators when disposed of in a toilet bowl.

EXAMPLE 4

Biodegradability

Tampon applicators prepared in accordance with the procedures of Example 1 were tested for their ability to support fungal growth. ASTM Standard G 21 was used for this test.

The experiment was performed in triplicate, along with negative and positive controls. An agar solution containing nutrient salts was placed into sterile Petri dishes to a depth of 3-6 mm and a three-inch (7.6-cm) portion of an applicator tube was placed onto the surface of the agar in each dish after the agar had partially solidified. An *Aureobasidium pullulans* fungus spore suspension was then used to inoculate the samples.

The Petri dishes were covered and then incubated for 21 days at 82-86 degrees F. (28-30 degrees C) and a relative humidity of not less than 85 percent. The level of growth on the applicators was evaluated after 7, 14, and 21 days of incubation using the following scale:

| Rating | Observed Growth on Specimen |
|--------|------------------------------|
| 0 | None |
| 1 | Trace (less than 10 percent) |
| 2 | Light Growth (10-30 percent) |
| 2 | Medium Growth (30-60 percent) |

-continued

| Rating | Observed Growth on Specimen |
|--------|------------------------------|
| 4 | Heavy Growth (greater than 60 percent) |

For the applicators of the invention, a full scale rating of 4 was observed after only one week. This result is considered to be strong evidence of the rapid biodegradability of the tampon applicators of the present invention.

Having thus described the invention, numerous changes and modifications thereof will be readily apparent to those having ordinary skill in the art without departing from the spirit and scope of the invention.

What is claimed is:

1. A tampon applicator comprising at least one elongated tubular member prepared from an injection-moldable or extrudable material which includes a poly(vinyl alcohol) which has been modified so that it is self-plasticizing, said tampon applicator being water-dispersible and biodegradable, in which the poly(vinyl alcohol) is represented by the following structural formula:

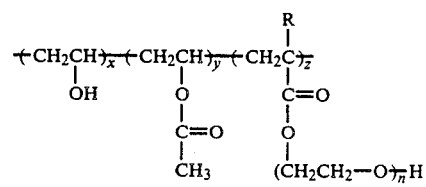

in which R is hydrogen or methyl, n is a number from 1-1,000, x is 50-99.9 mole percent, y is 0-50 mole percent, and z is 00.001-50 mole percent.

2. The tampon applicator of claim 1, in which the injection-moldable or extrudable material has a viscosity at 195 degrees C. of between about 2,500 and about 4,500 poise at a shear rate of 200 sec$^{-1}$ and of between about 500 and about 800 poise at a shear rate of 4,000 sec$^{-1}$.

3. The tampon applicator of claim 1, in which the injection-moldable or extrudable material includes a filler.

4. The tampon applicator of claim 1, in which the injection-moldable or extrudable material includes a pigment.

5. The tampon applicator of claim 1, in which the injection-moldable or extrudable material includes an odor masker.

6. The tampon applicator of claim 5, in which the odor masker is calcium carbonate.

7. The tampon applicator of claim 1, in which said applicator comprises a pair of telescoping tubes, at least one of which is prepared from said injection-moldable or extrudable material.

8. The tampon applicator of claim 7, in which the outer tube is prepared by injection molding and the inner tube is prepared by extrusion.

9. The tampon applicator of claim 1, in which the applicator has a wall thickness of 0.025 inches or less and wherein the applicator is substantially completely dispersed in stirred, room temperature water in less than two hours.

10. The tampon applicator of claim 2, in which the applicator has a wall thickness of 0.025 inches or less and wherein the applicator is substantially completely dispersed in stirred, room temperature water in less than two hours.

* * * * *